(12) United States Patent
Singhi et al.

(10) Patent No.: US 12,162,253 B2
(45) Date of Patent: Dec. 10, 2024

(54) THIN WALL LUBRICIOUS POLYETHYLENE LINERS

(71) Applicant: ZEUS COMPANY INC., Orangeburg, SC (US)

(72) Inventors: Bhavya Singhi, Columbia, SC (US); John Richard Campanelli, West Columbia, SC (US)

(73) Assignee: Zeus Company LLC, Orangeburg, SC (US)

( * ) Notice: Subject to any disclaimer, the term of this patent is extended or adjusted under 35 U.S.C. 154(b) by 0 days.

(21) Appl. No.: 17/896,188

(22) Filed: Aug. 26, 2022

(65) Prior Publication Data
US 2024/0066846 A1 Feb. 29, 2024

(51) Int. Cl.
| | | |
|---|---|---|
| *B32B 27/32* | (2006.01) | |
| *A61L 29/04* | (2006.01) | |
| *A61M 25/00* | (2006.01) | |
| *B29C 48/09* | (2019.01) | |
| *B29K 23/00* | (2006.01) | |
| *B29K 105/00* | (2006.01) | |

(Continued)

(52) U.S. Cl.
CPC ............ *B32B 27/32* (2013.01); *A61L 29/049* (2013.01); *A61M 25/0009* (2013.01); *B32B 1/08* (2013.01); *B32B 7/12* (2013.01); *B32B 27/08* (2013.01); *B29C 48/09* (2019.02); *B29K 2023/065* (2013.01); *B29K 2023/0683* (2013.01); *B29K 2105/0094* (2013.01); *B29K 2995/0063* (2013.01); *B32B 2250/242* (2013.01); *B32B 2270/00* (2013.01); *B32B 2307/538* (2013.01); *B32B 2307/54* (2013.01); *B32B 2307/732* (2013.01); *B32B 2535/00* (2013.01); *B32B 2597/00* (2013.01)

(58) Field of Classification Search
CPC .. B32B 27/32; B32B 1/08; B32B 7/12; B32B 27/08; B32B 2250/242; B32B 2270/00; B32B 2307/538; B32B 2307/54; B32B 2307/732; B32B 2535/00; B32B 2597/00; A61L 29/049; A61M 25/0009; B29K 2023/065; B29K 2023/0683; B29K 2105/0094; B29K 2995/0063
See application file for complete search history.

(56) References Cited

U.S. PATENT DOCUMENTS

| | | |
|---|---|---|
| 5,803,130 A | 9/1998 | Robben et al. |
| 9,175,111 B2 | 11/2015 | Kapur et al. |

(Continued)

FOREIGN PATENT DOCUMENTS

| | | |
|---|---|---|
| AU | 2017200223 B2 | 8/2018 |

OTHER PUBLICATIONS

English machine translation for CN110328942 (Oct. 15, 2019) (Year: 2019).*

(Continued)

*Primary Examiner* — Michael C Miggins
(74) *Attorney, Agent, or Firm* — Jessica L. Gorczynski; Womble Bond Dickinson (US) LLP

(57) ABSTRACT

The disclosure provides tubes including a blend of two or more polyethylenes. For example, the blend can comprise at least 80% by weight of one or more of LLDPE, LDPE, MDPE, and HDPE, and no more than 20% by weight of UHMWPE. Such tubes can have low average wall thicknesses, e.g., 0.1 mm or less, rendering them suitable for use as catheter liners.

22 Claims, 2 Drawing Sheets

(51) Int. Cl.
　　　*B32B 1/08*　　　(2006.01)
　　　*B32B 7/12*　　　(2006.01)
　　　*B32B 27/08*　　(2006.01)

(56) References Cited

U.S. PATENT DOCUMENTS

| | | |
|---|---|---|
| 10,646,704 B2 | 5/2020 | Bourgeois et al. |
| 2007/0178131 A1 | 8/2007 | Yamada et al. |
| 2021/0371632 A1* | 12/2021 | Soulages ................ C08L 23/04 |

OTHER PUBLICATIONS

PCT Search Report & Written Opinion dated Jan. 3, 2023 which issued in corresponding PCT Application No. PCT/US2022/042482.

Maa Toq, M et al. "Carbon Nano-tube-based Reinforced Polymers for Medical Applications: Improving Impact Strength of Polymer-Polymer Composites" vol. 2022, Article ID 1760198. Journal Of Nanomaterials. Online. Apr. 1, 2022; Entire Document; DOI: 10.1155/2022/1760198.

Kazmierska, K et al. "Determination of Urethral catheter surface lubricity" 2301-2306 . Journal of Material Science: Materials in Medicine. Online. Jul. 2008; Entire Document; DOI: 10.1007/s10856-007-3339-4.

* cited by examiner

THIN WALL LUBRICIOUS POLYETHYLENE LINERS

FIELD OF THE INVENTION

The present application relates generally to the field of tubes, such as for use as thin wall catheter liners, comprising two or more types of polyethylene resins and to methods and properties thereof, relating to such tubes.

BACKGROUND OF THE INVENTION

Vascular therapy uses minimally invasive, catheter-based procedures and specialized equipment and techniques. Catheters used in these procedures commonly employ a coating or liner on the inner wall to provide a lubricious inner surface. A lubricious inside diameter (ID) associated with these devices is beneficial in reducing friction against various catheter technologies such as stents, balloons, atherectomy or thrombectomy devices as they are pushed through the tight confines of the catheter lumen. If the catheter ID is not of sufficient lubricity, devices such as stents can cause the liner to collapse in an accordion-like manner as the devices are pushed through the catheter lumen. The effect of increased lubricity of the catheter ID is a reduced deployment force of catheter devices as they are passed through the lumen, increasing the likelihood of a successful procedure. The mechanical properties of a catheter liner are also extremely important. For example, high tensile and yield strength may be required when certain devices (e.g., flow diversion tubes, embolization coils, aneurysm bridging devices, scaffolding and thrombectomy devices) are passed through microcatheters in a compressed state. The compressed shape exerts an outward radial force, which causes friction with the ID, commonly making delivery of the device through the lumen difficult. On the other hand, high flexibility of a liner is often desirable when catheters must pass through vasculature that involves sharp twists and turns (e.g., cerebral vasculature and below-the-knee (BTK) applications).

Among the various materials that have been pursued as inner wall (base liner) materials for use, e.g., within such catheter devices is polytetrafluoroethylene (PTFE) due to its excellent chemical resistance, high temperature resistance, biocompatibility and very low coefficient of friction/high lubricity. One major drawback of PTFE is that it is not radiation stable. Radiation sterilization (i.e., gamma rays or electron beams) is one of the most widely used and safe sterilization process for medical devices. Radiation sterilization improves the manufacturability of catheters as it can be quickly performed in the manufacturing line, while an alternative ethylene oxide gas (ETO) sterilization procedure, typically used with PTFE-lined catheters, requires storage for up to 48 hours to allow the gas to diffuse out of the sterilized equipment. Also, ETO requires careful handling because of its flammability and toxicity. Strict handling requirements and a technically complex sterilization process makes ETO sterilization technique often undesirable. In recent times, medical regulatory organizations worldwide have also been encouraging the medical industry to minimize or replace the use of ETO with alternative sterilization methods.

Some materials which can be used as alternatives to PTFE and which are also stable under irradiation utilize polymers such as Nylon and Pebax®; however, these polymers are not widely acceptable as catheter materials due to their relatively higher coefficient of friction. Thus, the advantage of irradiation stability provided by Nylon and Pebax® is offset by lower lubricity in comparison to PTFE. Polyethylene materials, especially the higher density grades, have a significantly lower coefficient of friction than that of other commonly extruded polymers such as polypropylene. Like Nylon and Pebax, polyethylene is radiation stable, so a catheter liner made from polyethylene materials may be sterilized using irradiation.

Another disadvantage of PTFE-based lubricious liners is the hydrophobicity of the inner surface. In certain applications, high lubricity of a wetted inner surface of the liner is required—such as when injecting a saline based solution through a catheter. The hydrophobic nature of PTFE prevents adequate wetting of the surface and tends to reduce the lubricity of the PTFE surface.

Typically, for increased wet lubricity of polyethylene liners, a hydrophilic lubricious coating is applied to the inner surface of the substrate. These hydrophilic coatings are used to lower the coefficient of friction for medical instruments such as catheters, probes or feeding tubes. Some of the commonly known lubricant coatings which are applied to medical device surfaces include formulations made with polyvinylpyrrolidone, polyurethane, acrylic polyester, vinyl resin, fluorocarbons, silicone rubber, and/or combinations of these substances. For example, Micklus et al. (U.S. Pat. Nos. 4,100,309 and 4,119,094) describes a hydrophilic coating made with a polyvinylpyrrolidone-polyurethane interpolymer formed using polyisocyanate. Ratner et al. (U.S. Pat. No. 3,939,049) explains a method for lubrication by grafting hydrogels to polymeric materials using radiation. Hungton et al. (U.S. Pat. No. 3,975,350) relates to hydrophilic polyurethane polymers for use as lubricants. Storey et al. (U.S. Pat. No. 3,987,497) relates to a tendon prosthesis having a lubricant hydrogel coating.

However, the major disadvantage exhibited by such hydrophilic lubricious coatings is that the processes developed for applying such coatings to such medical instruments comprise numerous steps, which are time consuming and as a result thereof; large scale production is less financially beneficial. Other disadvantages of such lubricant coatings may include insufficient lubricity, lack of durability which is characteristic of silicone or fluorocarbon based coatings, use of hazardous solvents or unstable reactive materials in their manufacturing. Lubricants which are manufactured for medical applications from unstable reactive material often require the coating solutions to be prepared more frequently to be useful thereby increasing waste and expense. Likewise, lubricants used for medical applications made with hazardous solvents are undesirable due to concerns over patient toxicity and OSHA regulations. Additionally, lubricant coatings for medical devices used during invasive procedures sometimes making the body susceptible to infections and/or thrombogenic reactions, have failed to incorporate pharmaceutically acceptable levels of antimicrobial and anti-thrombogenic compounds.

In order to solve these and other potential disadvantages of lubricant-based hydrophilic coatings such as those of the above-cited patents, an alternate method for producing thin walled lubricious polyethylene liners is needed that when wetted has sufficient lubricity to be useful in the medical device field. The lubricious polyethylene liner must be capable of adhering to a wide variety of substrates and resist wet abrasion. Further, it would be beneficial to have such a lubricious hydrophilic polyethylene liner produced in fewer number of processing steps.

SUMMARY OF THE INVENTION

The present disclosure provides thin-walled lubricious polyethylene (PE) tubes, products incorporating such tubes, and methods for producing and using such tubes and products. The disclosed PE tubes generally comprise more than one PE and can be produced by melt extrusion of polyethylene blends. Exemplary average wall thicknesses of the tubes provided herein can be less than 0.100 mm (preferably less than 0.050 mm), with moderate to high machine direction orientation of polyethylene polymer. Depending on the formulation of the polyethylene blend, in some embodiments, the tubes can have high flexibility while having internal tube surfaces exhibiting high lubricity and abrasion resistance. The combination of properties exhibited by the disclosed tubes, in various embodiments, can render them particularly suitable for use within catheters, including within catheters designed for flexibility, as the thin wall thicknesses and low modulus values of the disclosed tubes provide for a significantly flexible tube/liner product. Moreover, the polyethylene tubes of the current disclosure are also radiation resistant and sterilizable (unlike PTFE liners). In some embodiments, the tubes are oriented in the machine and/or transverse direction, which can afford enhanced mechanical, thermal and barrier properties. Additionally, the polyethylene tubes of this invention can be used as liners for metallic tubes, such as for laser-cut hypotubes.

The invention includes, without limitation, the following embodiments.

Embodiment 1: A tube comprising a blend of two or more polyethylenes, the tube having an average wall thickness of 0.1 mm or less, and the tube comprising a blend of: UHMWPE, in an amount of no more than 20 percent by weight; and at least 80 percent by weight of at least one second polyethylene resin selected from the group consisting of LLDPE, LDPE, MDPE and HDPE.

Embodiment 2: The tube of Embodiment 1, in the form of a tube over a wire or mandrel.

Embodiment 3: The tube of any of Embodiments 1-2, wherein the average wall thickness of the tube is less than 0.075 mm.

Embodiment 4: The tube of any of Embodiments 1-3, wherein the average wall thickness of the tube is less than 0.050 mm.

Embodiment 5: The tube of any of Embodiments 1-4, wherein the tube comprises no more than 10 percent by weight UHMWPE.

Embodiment 6: The tube of any of Embodiments 1-5, wherein the tube comprises no more than 5 percent by weight UHMWPE.

Embodiment 7: The tube of any of Embodiments 1-6, wherein the at least one second polyethylene resin comprises HDPE.

Embodiment 8: The tube of any of Embodiments 1-7, wherein the two or more polyethylenes comprise at least one chemically modified polyethylene.

Embodiment 9: The tube of Embodiment 8, wherein the chemically modified polyethylene is maleic anhydride grafted polyethylene.

Embodiment 10: The tube of any of Embodiments 1-9, further comprising one or more additives selected from the group consisting of one or more antioxidants, antimicrobials, processing aids, colorants, slip aids, and combinations thereof.

Embodiment 11: The tube of any of Embodiments 1-10, wherein the tube further comprises a continuous layer on an inside surface or an outer surface, the continuous layer comprising a second blend, wherein the second blend comprises a chemically modified polyethylene.

Embodiment 12: The tube of Embodiment 11, wherein the tube comprises a first continuous layer on the inside surface and a second continuous layer on the outer surface, the first and second continuous layers being the same or different.

Embodiment 13: The tube of any of Embodiments 1-12, wherein the tube exhibits a coefficient of friction in air at 23° C. of 0.2 or less.

Embodiment 14: The tube of any of Embodiments 1-13, wherein the tube exhibits a coefficient of friction in saline at 23° C. of 0.2 or less.

Embodiment 15: The tube of any of Embodiments 1-14, wherein the tube exhibits a coefficient of friction in saline at 23° C. of 0.1 or less.

Embodiment 16: A medical device comprising the tube of any of Embodiments 1-15.

Embodiment 17: A method of preparing the tube of any of Embodiments 1-15, comprising: providing the two or more polyethylenes; and extruding the two or more polyethylenes through an extruder to form the tube.

Embodiment 18: The method of Embodiment 17, wherein the two or more polyethylenes are in the form of a blended material.

Embodiment 19: The method of Embodiment 18, wherein the blended material has an MFI of 3.0 g/10 min or less.

Embodiment 20: The method of any of Embodiments 18-19, wherein the blended material has an MFI of 2.5 g/10 min or less.

Embodiment 21: The method of any of Embodiments 18-20, wherein the blended material has a calculated density of 0.94 g/cm$^3$ to 0.96 g/cm$^3$.

Embodiment 22: The method of Embodiment 17, wherein the two or more polyethylenes are individual components that are combined immediately prior to the extruding.

These and other features, aspects, and advantages of the disclosure will be apparent from a reading of the following detailed description together with the accompanying drawings, which are briefly described below. The invention includes any combination of two, three, four, or more of the above-noted embodiments, as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

In order to provide an understanding of the embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

Figure 1:
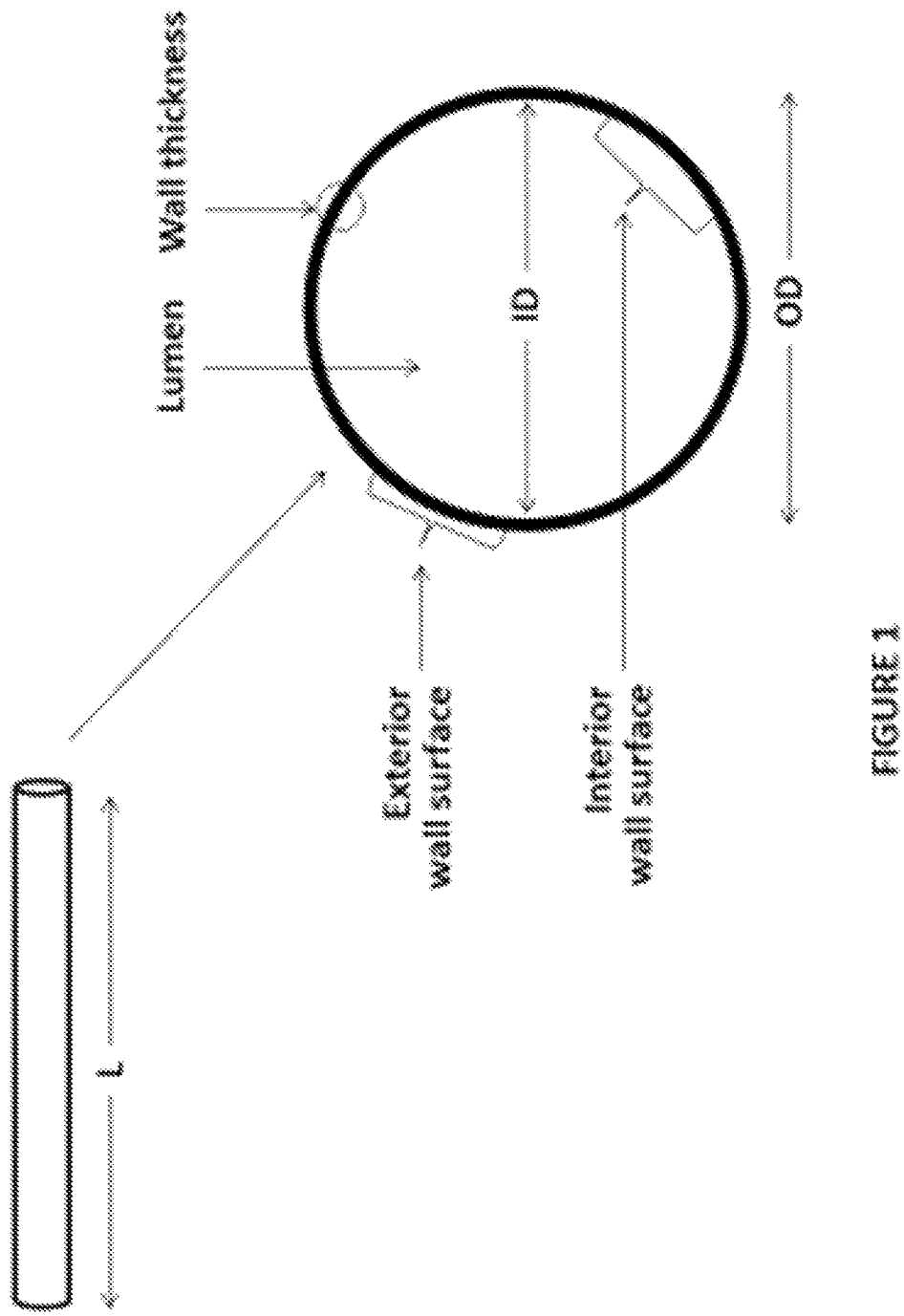
FIG. 1 is a general schematic of a tube of the present disclosure, with relevant parameters, and an expanded schematic of one cross-sectional end face of the tube.

A general schematic of a tube is shown in FIG. 1. The tube is generally cylindrical in shape. "L" indicates the length of the tube as produced, which can be processed, e.g., cut, to provide tubes of desired length "l" (not shown). The expanded region at the right of FIG. 1 is a cross-sectional view of the interior of the tube. As shown, the "lumen" is an interior region of the tube, i.e., an open channel/cavity (through which, e.g., a catheter device may be passed). The inner diameter of the tube, shown as "ID" is the average distance from a point on the interior wall of the tube to the opposite/farthest point on the interior wall of the tube. The outer diameter of the tube, shown as "OD" is the average distance from a point on the outer wall of the tube through the lumen of the tube to the opposite/farthest point on the outer wall of the tube. As such, half of the OD value minus the ID value provides the average wall thickness of the tube. A representative "wall thickness," "interior wall surface," and "exterior wall surface" of the tube are shown in FIG. 1. The present disclosure provides thin wall, lubricious polyethylene tubes. By "polyethylene tubes" is meant that the tube consists primarily of one or more polyethylenes, e.g., two or more polyethylenes.

Figure 2B:
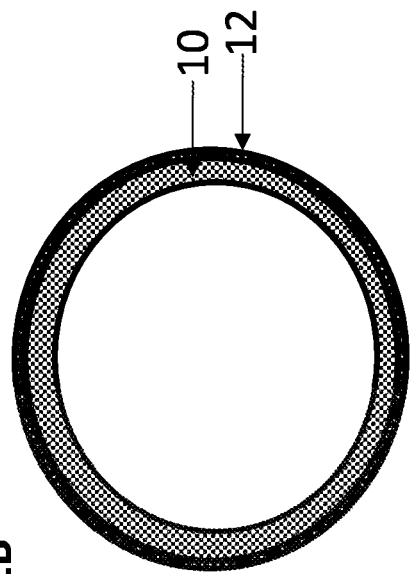
FIGS. 2A, 2B, 2C, and 2D are general schematics of cross-sections of tubes according to various embodiments of the disclosure.
Figure 2D:
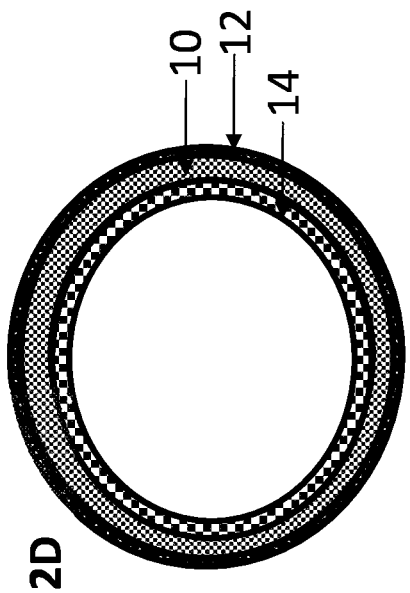
Figure 2A:
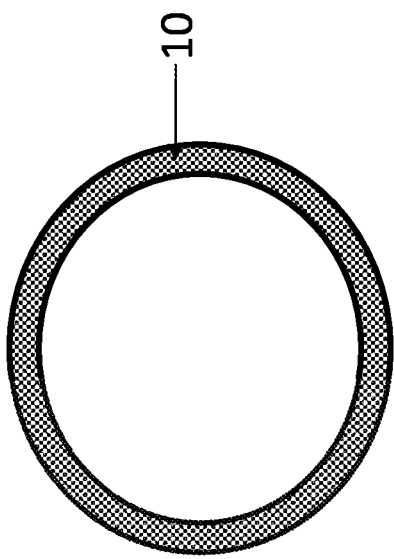
Figure 2C:
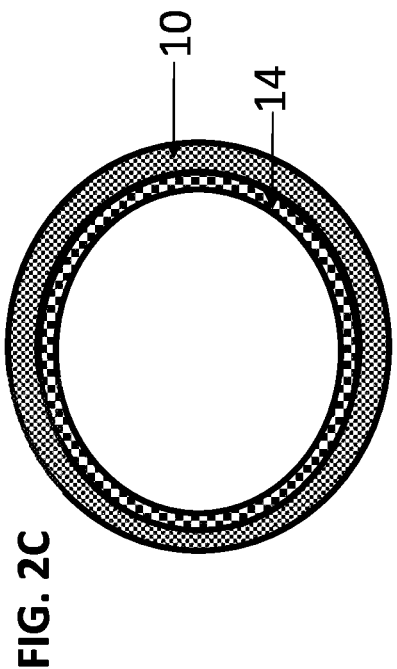

In some embodiments, tubes as provided herein are substantially homogeneous in composition throughout the wall and/or length of the tube (e.g., as shown in FIG. 2A, which provides a cross-section of a tube comprising polyethylene blend 10). In some non-limiting embodiments, tubes as provided herein are substantially homogeneous with the exception that the inner and/or outer surface of the tube may comprise a different material. For example, FIG. 2B is a cross-section of a tube comprising polyethylene blend 10, with a different material 12 as a layer on the outer surface of blend 10. FIG. 2C is a cross-section of a tube comprising polyethylene blend 10, with a different material 14 as a layer on the inner surface of blend 10. FIG. 2D is a cross-section of a tube comprising polyethylene blend 10, with a different material 12 as a layer on the outer surface of blend 10 and a different material 14 as a layer on the inner surface of blend 10 (where the composition of 14 can be the same as or different than that of 12).

Typically, the composition of 10 comprises a blend of two or more polyethylenes. Suitable polyethylenes include, but are not limited to, low density polyethylene ("LDPE"), linear low density polyethylene ("LLDPE"), medium density polyethylene ("MDPE"), high density polyethylene ("HDPE"), ultra high molecular weight polyethylene ("UHMWPE"), and chemically modified polyethylenes, e.g., modified LDPE or modified LLDPE (or in some cases modified HDPE), including grafted polyethylenes. Suitable chemically modified polyethylenes include, but are not limited to, anhydride-grafted LDPE, LLDPE, or HDPE, such as maleic anhydride-grafted LDPE, LLDPE, or HDPE). Other chemically modified polyethylenes that can be suitably included in 10 include, but are not limited to, ethylene vinyl acetate copolymers, ethylene methyl acrylate copolymers, ethylene acrylic acid copolymers, ethylene methacrylic acid copolymers, ethylene-acrylic ester-maleic anhydride terpolymer, and the like. Such chemically modified polyethylenes generally serve as tie resins and thus can be referred to as such in some places herein. In some embodiments, 10 may optionally further comprise one or more additives such as one or more antioxidants, antimicrobials, processing aids, slip aids and colorants, as well as other particulates designed to impart specific properties to the tubes.

In one embodiment, 10 comprises: a) HDPE, LDPE, or LLDPE; and b) UHMWPE. The amount of HDPE in some such embodiments is about 50 to about 90 percent by weight, preferably from about 65 to about 85 percent by weight, and more preferably from about 70 to about 80 percent by weight, based on the total weight of the tube. The amount of LDPE in some such embodiments is from about 5 to about 40 percent by weight, preferably from about 10 to about 25 percent by weight, and more preferably about 15 to about 25 percent by weight, based on the total weight of the tube. The amount of LLDPE in some such embodiments is less than 30 percent by weight, preferably less than 20 percent by weight, and more preferably less than 15 percent by weight, based on the total weight of the tube. In certain embodiments, 10 comprises: a) HDPE and b) UHMWPE (and can optionally further comprise one or more of LDPE and LLDPE). All such embodiments may optionally further comprise one or more tie resins.

The amount of UHMWPE in some such embodiments is less than 20 percent by weight, preferably less than 10 percent by weight, and more preferably less than 5 percent by weight, based on the total weight of the tube. For example, a given tube may comprise about 1 to about 20 percent by weight of UHMWPE, about 1 to about 10 percent, about 1 to about 5 percent, about 2 to about 20 percent, about 2 to about 10 percent, about 5 to about 20 percent, or about 5 to about 10 percent of UHMWPE. The inclusion of UHMWPE can impart roughness to the tube. The roughness can be on the inner and/or outer wall surfaces of the tubes. The degree of roughness can be varied by changing the concentration of UHMWPE in the tube as well as by varying the size of the UHMWPE particles used to produce the tube. The degree of roughness can, in some embodiments, affect the physical, mechanical, and/or thermal properties of the tube, such as lubricity, tenacity, modulus, and the like. The degree of roughness, particularly on the outer surface of the tube, can also have an effect on the bondability of the polyethylene blend liners with catheter jackets.

Chemically modified polyethylenes, where included, are generally present in amounts up to about 50% by weight, e.g., 0% to about 50% by weight, about 0% to about 25% by weight, about 5% to about 50% by weight, about 5% to about 25% by weight, or about 25% by weight to about 50% by weight.

The two or more different polyethylenes within 10 may differ in composition, grade, molecular weight, or any combination thereof. The amount and grade(s) of polyethylenes in the disclosed tubes can vary, which can result in different thermal, mechanical and structural properties of the tubes.

For example, in some embodiments, tubes comprising one or more chemically modified polyethylenes (tie layer resins) generally exhibit increased hydrophilicity (as compared to comparable tubes not comprising any chemically modified polyethylenes), including increased hydrophilicity of the inner wall surface of the tube, rendering such tubes more suitable for applications requiring high lubricity of a wetted inner wall surface (e.g., for certain catheter uses). In some embodiments, the polyethylene tubes provided herein have low coefficients of friction (COFs). For example, in some embodiments, the COF of a polyethylene tube as provided herein is about 0.2 or less or about 0.1 or less in saline at 23° C. The inner surface of a hydrophilic liner can be wetted by water or saline to improve the overall lubricity of the inner surface by providing a tribological layer that lowers the coefficient of friction (COF). In some embodiments, such tubes comprising one or more modified and/or grafted polyethylenes comprise sites for chemically bonding the outer wall surface to an outer layer such as nylon, polyether-block-amide (PEBA), which is advantageous for the use of the tubes as catheter liners.

In some embodiments, the disclosed tubes have thin walls, e.g., having walls of average thickness of less than about 0.100 mm, preferably less than about 0.075 mm and, more preferably less than 0.050 mm. Some such thin walls have average thicknesses of about 0.010 mm to about 0.10 mm, about 0.010 mm to about 0.075 mm, or about 0.010 mm to about 0.050 mm. In some embodiments, the disclosed polyethylene tubes do not require additional surface treatment or tie layers to enhance bonding between the outer surface of the polyethylene tube and an adjacent material (e.g., including, but not limited to, a jacket material, such as employed in catheters).

The disclosure also provides products such as medical catheters that include a polyethylene tube as described herein. For example, in some embodiments, a medical catheter in the form of a three-layer catheter is provided, comprising, as an innermost layer, a polyethylene tube as provided herein. For such applications, the polyethylene tube generally has an average wall thickness between about 0.025 mm and about 0.070 mm and an inside diameter (ID) between about 0.380 mm and about 4.300 mm. The polyethylene tube is enveloped by a braided layer, and a jacket encloses the braided layer. In some embodiments, such a construct comprises an additional tie layer to enhance the bonding between the polyethylene tube and the jacket, further increasing the size and thickness of the catheter. In some embodiments, as referenced above, no tie layer is required, and in some embodiments, no surface treatment of the polyethylene tube is required to produce a suitable jacketed construct useful in a medical catheter.

Methods of producing polyethylene tubes as described herein can vary. According to certain embodiments, a melt-processable blend of two or more polyethylenes as described herein above is first prepared.

In such embodiments, two or more polyethylene resins described herein above are selected and processed into the form of a blend using typical melt processing apparatus and under typical melt processing conditions. Preferably, an intimate blend of the two or more polyethylene resins is formed in the molten state in an extruder (e.g., an inter-meshing co-rotating twin screw extruder, although other types of twin screw extruders can be used). The twin screw extruder preferably has a length to diameter ratio at least about 20:1, more preferably at least about 30:1 and most preferably at least about 40:1. The mixture of polyethylene resins is passed through the extruder to form an extrudate. As the extrudate exits the twin screw extruder, it is generally in the form of a monofilament blend and can be cut, e.g., into pellets. The pellets can be subsequently fed into the throat of a single screw extruder and extruded into a tubular structure from the single screw melt extruder. In some such embodiments, the melt flow index (MFI) of the blend is 3.0 g/10 min or less or 2.5 g/10 min or less. The blend can also be defined, in some embodiments, by its calculated density. For example, in some embodiments, the blend has a calculated density of 0.94 g/cm$^3$ to 0.96 g/cm$^3$.

In an alternative embodiment, the components of the polyethylene blend can be individually fed in the correct proportions directly into the feed throat of a single screw extruder with mixing screw and extruded into a tubular structure.

In the embodiments described herein above, the hot tubular extrudate exiting the single screw extruder is pulled and stretched to the desired size as it emerges from the extruder to give 10. Typically, upon emerging from the extruder, it passes into a cooling chamber, which is preferably at a temperature between 5° C. and 25° C.

In some embodiments, tubes are provided by extruding the material over a wire or mandrel (which can be metallic or non-metallic, e.g., polymeric, such as polytetrafluoroethylene (PTFE) or polyetherether ketone (PEEK)) The mandrel can be smooth or textured. For example, in some embodiments, a textured mandrel is employed, comprising PTFE and one or more fillers such as glass beads, glass bubbles, clay, silica, silicates, metal oxides, metal hydroxides, and combinations thereof. A non-limiting textured mandrel encompassed by the present disclosure (e.g., as referenced in the example herein), can have a surface roughness that is characterized by: a minimum average surface roughness, Ra, of 0.50 μm; and/or a minimum root mean square (RMS) surface roughness, Rq, of 0.75 μm (including, e.g., embodiments wherein the surface roughness is characterized by both a minimum average surface roughness, Ra, of 0.50 μm; and a minimum RMS surface roughness, Rq, of 0.75 μm). Extruding over a mandrel (metallic or non-metallic) can affect some physical, mechanical or thermal properties of the resulting tube, such as lubricity, tenacity, modulus, etc. Extruding over a mandrel can could also have an effect on the bondability of the outer surface of the tube with catheter jackets.

During extrusion processing, molecular/chain orientation can be imparted into the extruded product (e.g., the final part) based on the drawdown of the material. The drawdown and other parameters of the extrusion can be adjusted/modified as known in the art to achieve the desired result (e.g., the desired orientation). Orientation imparted into a material is known to impact tensile properties—especially the modulus, tensile strength, and elongation. With the changes noted in modulus, the COF may be altered as well. Generally, increasing the drawdown increases the axial orientation of the polymer, thereby increasing the modulus and tensile strength and reducing the elongation & COF. Again, one of skill in the art can modify the drawdown to alter the modulus, tensile strength, elongation, and/or COF to produce a tube with suitable physical properties for the intended end use.

In polyethylene blends containing tie resins, the amount of functional groups such as maleic anhydride present on the inner and outer wall surfaces of the tubes could potentially be varied by changing the mandrel material (such as using a PTFE-coated mandrel). The migration of polymers containing functional groups to the inner and outer wall surfaces would also be dependent on the overall concentration of these groups within the formulation to be extruded. The variation in the amount of tie resin on the inside and outside wall surfaces of the tubes could affect physical, mechanical or thermal properties, especially the surface tension and lubricity of each wall surface. It could also affect the bondability of the polyethylene blend liners with catheter jackets.

The extrudate can optionally be further processed, e.g., by cutting the long tube into shorter lengths as desired, e.g., for certain specific applications. The extruded tubes can be subjected to radiation such as e-beam or gamma processing (e.g., with a dosage of 50 kGy to 15 MGy). The radiation treatment can alter the polymeric chain structure of the tubes and affect some physical, mechanical or thermal properties of the tubes, such as lubricity, tenacity, modulus, etc. Typically, radiation treatment can impart crosslinking in polyethylene chains, which increases the modulus and tensile strength. One of skill in the art is aware of such radiation treatments and can select appropriate methods and parameters to modify the tube as desired.

In some embodiments, a modified/grafted polyethylene tie layer resin is incorporated within the blend referenced herein above (and thus incorporated within 10). In some embodiments, other additives are also incorporated within the blend referenced herein above (and thus incorporated within 10). As such, the method can further comprise blending one or more tie layer resins and/or one or more additives with the two or more polyethylene resins or can further comprise individually adding such components directly into the feed throat of a single screw extruder with mixing screw and extruding them along with the one or more polyethylene resins into tubular structure 10.

Alternatively (or in addition), the optional inclusion of modified and/or grafted polyethylene tie layer resin within the final tube can be accomplished by co-extrusion. In such embodiments, the modified and/or grafted polyethylene tie layer resin is coextruded with the one or more polyethylenes referenced above, with or without a mandrel (metallic/non-metallic), to form the inner wall surface (14) and/or outer wall surface (12) of the tube (see FIGS. 2B, 2C, and 2D). In such embodiments, these optional resins may also be blended with other grades of polyethylenes such as LDPE, LLDPE, MDPE, HDPE and/or UHMWPE and coextruded with the one or more polyethylenes, with or without a mandrel (metallic/non-metallic), to form the inner wall surface (14) and/or outer wall surface (12) of the tube (see FIGS. 2B, 2C, and 2D). The coextrusion process can affect some physical, mechanical or thermal properties of the polyethylene blend tubing, such as lubricity, tenacity, modulus, etc. Coextruding could also have an effect on the bondability of the polyethylene tubes with catheter jackets applied thereover.

In further embodiments, catheter jacket materials such as nylon, PEBA, etc., can also be co-extruded with the one or more polyethylenes as provided herein.

For building catheters using the disclosed polyethylene tubes, instruments such as the Beahm 810A vertical laminator can be used. The polyethylene tubes provided herein can be bonded with catheter jackets made with materials such as PEBA, nylon, polyurethane, and the like. The polyethylene tubes provided herein can be stretched to reduce the wall thickness of the tube, without lowering the bondability of the surface and then used to build catheters. The degree of stretching of the tube can affect some physical, mechanical or thermal properties of the tube, such as lubricity, tenacity, modulus, etc. Typically, increasing the degree of stretching increases the axial orientation of the tubes, thereby increasing the modulus and tensile strength and reducing the elongation.

Built catheters and catheter components such as liners and jackets can be tested using an interventional device testing equipment such as the IDTE3000 from MSI which can measure and record device performance features such as pushability, flexibility, torqueability, etc.

EXPERIMENTAL

Embodiments of the present disclosure are more fully illustrated by the following examples, which are set forth to illustrate aspects of the present disclosure and are not to be construed as limiting thereof. Unless otherwise noted, all parts and percentages are by weight.

Test Methods

An Instron 5965 dual column mechanical tester running Bluehill 3 v3.73.4823 operating software was used to determine the tensile properties of the polyethylene tubes. The test was performed at room temperature (23° C.) at a rate of 508 mm/min using a 1 kN load cell set to a 50.8 mm gage length. An environmental chamber was used to measure tensile properties at an elevated temperature of 120° C. with a 1 kN load cell. Crosshead travel limit within the environmental chamber was 26.7 mm, therefore the gage length was reduced to 2.54 mm and the crosshead speed reduced to 25.4 mm/min to match the nominal strain rate of 50.8 mm gage length @ 508 mm/min testing at room temperature. At least 3 specimens were tested for each blend and temperature, and the average results are reported in Table 2.

A TA instruments Q800 DMA with the film tension fixture was used to determine the thermo-mechanical properties of the polyethylene blend tubing. The main property of interest was storage modulus (E'). A temperature scan was performed from −100° C. to 130° C. with an isothermal hold for five minutes at −100° C. The sample was heated at a constant rate of 3° C./min while being displaced at a constant amplitude of 15 µm with a fixed frequency tensile oscillation of 1 Hz. The resulting DMA data was imported into TA instruments TRIOS software v4.3, and the average values of the storage modulus at 23° C. and 40° C. are listed in Table 2.

A TA instruments Discovery Hybrid Rheometer (DHR-3) rheometer with the tribo-rheometer accessory was used to determine the tribological properties of the polyethylene blend tubing. The main property of interest during this test was the coefficient of friction (COF). The samples were prepared by attaching three tubing sections of 5 mm×16.5 mm each to the three teeth of the half-ring for use with a Ring-on-Plate tribo-rheometry fixture. The ring with mounted samples was then attached to the ring-on-plate upper-geometry holder and lowered to have the samples contact a mirror-finish stainless steel plate at the specified axial force. Tribological tests were performed at room temperature (23° C.) and 40° C., from sliding speeds of 750 µm/s to 7650 µm/s under an axial load of 1N. Additional tribological tests were performed in a saline bath at room temperature (23° C.) and 40° C., from sliding speeds of 750 µm/s to 7650 µm/s under an axial load of 1N. Minimum COF over the stated range in sliding speed was calculated by the TA instruments TRIOS software v4.3. Three samples were tested for each blend and temperature, and the averages are listed in Table 2.

A ThermoScientific Nicolet iS50 FTIR equipped with a diamond crystal ATR was used to acquire infrared spectra of the polyethylene blend tubes and polyethylene melt plaques per ASTM E1252. The FTIR test was performed on the outside and inside surfaces of the tubing samples and both surfaces of the plaques. The amount of maleic anhydride present in the polyethylene tubes and plaques prepared from blends with different concentrations of tie resin was quantified using peak height ratios (Maleic Anhydride Grafting on EPDM: Qualitative and Quantitative Determination, 1999). The $CH_2$ band at 1460 cm$^{-1}$, present in all polyethylene resins and the C=O stretching band at 1780 cm$^{-1}$, characteristic of maleic anhydride, were used for quantification. The ratio of peak heights ($h_{1780}/h_{1460}$) for the two bands can be used to quantitatively compare the amount of maleic anhydride present in the samples. The ratios are listed in Table 3 and 4.

Polyethylene tubes and plaques were assessed for contact angle on a Tantec Inc. CAM-PLUS Contact Angle Meter using half-angle method per ASTM D7334. At least 3 readings were taken for each sample on the outer and inner surfaces of the tubes and both surfaces of the plaques. The results are listed in Table 2 and 4.

A Dynisco LMI4003 Melt Indexer was used to measure the melt flow index (MFI) of the resin blends. Standard ASTM Test Method D1238 was used at test conditions of 190° C. and 2.16 kg.

A Mitutoyo Surftest SJ-410 Profilometer was used to measure the surface roughness of the outer surface of the polyethylene tubing samples, with λs=2.54 mm. Five readings were taken for each sample. The average values are listed in Table 2.

The density of the polyethylene blends was calculated using the equation below, wherein, $m_a$ = Mass of resin A $\quad$ $m_a$ = Mass of resin A $\rho_a$ = Density of resin A $\quad$ $\rho_b$ = Density of resin B $\rho_c$ = Calculated density of blend of resins A and B $$\rho_c = \frac{m_a + m_b}{\frac{m_a}{\rho_a} + \frac{m_b}{\rho_b}}$$

A Thermo Scientific Heratherm oven was used to build catheters using the polyethylene blend tubing as liners and PEBA tubing as jackets. The tubing samples were slid over a PTFE mandrel followed by sliding over a PEBA tube wherein the ID of the PEBA tube is slightly greater than the OD of the polyethylene blend tubing. Finally, an FEP heat shrink tube was used to cover the catheter assembly in order to produce a uniformly bonded catheter. The heat shrink covered catheter assembly was kept in the oven at a temperature between 210-220° C. for five minutes. After taking the samples out of the oven, they were left at room temperature to cool. The heat shrink cover and the PTFE mandrel were both removed from the catheter assembly and the bonded catheter was tested for peel resistance to evaluate bondability.

An Instron 5965 dual column mechanical tester running Bluehill 3 v3.73.4823 operating software was used to determine the peel resistance of the polyethylene tubes bonded to PEBA catheter jackets. The test method used was a modification of ASTM D1876 (T-Peel Test), wherein the laminated test sample of the ASTM standard was a bonded catheter tube split in half. The polyethylene liner was gripped on one side and the PEBA jacket was gripped on the other. The test was performed at room temperature (23° C.) at a rate of 1 in/s using a 1 kN load cell set to a 25.4 mm gage length. At least 3 specimens were tested for each catheter type and the average results are reported in Table 3.

Polyethylene Blend Tubing Examples

Example 1

Polyethylene blend tubing with 89 wt % HDPE 1/9 wt % Tie Resin 1/2 wt % UHMWPE, was melt extruded to an OD of 1.880 mm and a wall thickness of 0.030 mm. Testing for the tubes was conducted using the methods described above. The average values are reported in Table 2.

Example 2

Polyethylene blend tubing with 89 wt % HDPE 1/9.9 wt % HDPE 2/1.1 wt % UHMWPE, was melt extruded to an OD of 1.850 mm and a wall thickness of 0.035 mm. Testing for the tubes was conducted using the methods described above. The average values are reported in Table 2.

Example 3

Polyethylene blend tubing with 71.2 wt % HDPE 1/20 wt % HDPE 2/7.2 wt % Tie Resin 1/1.6 wt % UHMWPE, was melt extruded to an OD of 1.830 mm and a wall thickness of 0.036 mm. Testing for the tubes was conducted using the methods described above. The average values are reported in Table 2.

Example 4

Polyethylene blend tubing with 48.75 wt % HDPE 1/48.75 wt % HDPE 3/2.5 wt % UHMWPE, was melt extruded to an OD of 1.800 mm and a wall thickness of 0.036 mm. Testing for the tubes was conducted using the methods described above. The average values are reported in Table 2.

Example 5

Polyethylene blend tubing from Example 4 was irradiated with ebeam for total dosage of 10 MGy. Testing for the tubes was conducted using the methods described above. The average values are reported in Table 2.

Example 6

Polyethylene blend tubing with 68 wt % HDPE 1/12 wt % HDPE 2/8.5 wt % Tie Resin 2/8.5 wt % LDPE/3 wt % UHMWPE, was melt extruded to an OD of 1.900 mm and a wall thickness of 0.030 mm. Testing for the tubes was conducted using the methods described above. The average values are reported in Table 2.

Polyethylene Blend Catheter Examples

Example 7

Polyethylene blend tubing with 72 wt % HDPE 1/18 wt % HDPE 3/8 wt % Tie Resin 2/2 wt % UHMWPE, was melt extruded to an OD of 1.850 mm and a wall thickness of 0.038 mm. The polyethylene tubes were used to build a catheter and tested for bondability using the methods described above. The average values are reported in Table 3.

Example 8

Polyethylene blend tubing with 64 wt % HDPE 1/18 wt % HDPE 3/16 wt % Tie Resin 2/2 wt % UHMWPE, was melt extruded to an OD of 1.830 mm and a wall thickness of 0.038 mm. The polyethylene tubes were used to build a catheter and tested for bondability using the methods described above. The inner and outer surfaces of the polyethylene tubing samples were also tested on FTIR. The average values are reported in Table 3.

Example 9

Polyethylene blend tubing from Example 8 was stretched 23% over a PTFE mandrel by heating the tubing samples to 115-120° C. The stretched polyethylene tubes were used to build a catheter and tested for bondability using the methods described above. The average values are reported in Table 3.

Example 10

Polyethylene blend tubing from Example 8 was stretched 45% over a PTFE mandrel by heating the tubing samples to 115-120° C. The stretched polyethylene tubes were used to build a catheter and tested for bondability using the methods described above. The average values are reported in Table 3.

Example 11

Polyethylene blend tubing with 64 wt % HDPE 1/18 wt % HDPE 3/16 wt % Tie Resin 2/2 wt % UHMWPE, was melt extruded over a PTFE mandrel to an OD of 1.750 mm and a wall thickness of 0.036 mm. The polyethylene tubes were used to build a catheter and tested for bondability using the methods described above. The inner and outer surfaces of the polyethylene tubing samples were also tested on FTIR. The average values are reported in Table 3.

Example 12

Polyethylene blend tubing with 74 wt % HDPE 1/24 wt % Tie Resin 2/2 wt % UHMWPE, was melt extruded to an OD of 1.830 mm and a wall thickness of 0.038 mm. The polyethylene tubes were used to build a catheter and tested for bondability using the methods described above. The average values are reported in Table 3.

Example 13

Polyethylene blend tubing with 52.5 wt % HDPE 1/15.75 wt % HDPE 3/30 wt % Tie Resin 2/1.75 wt % UHMWPE, was melt extruded to an OD of 1.800 mm and a wall thickness of 0.041 mm. The polyethylene tubes were used to build a catheter and tested for bondability using the methods described above. The inner and outer surfaces of the polyethylene tubing samples were also tested on FTIR. The average values are reported in Table 3.

Example 14

Polyethylene blend tubing with 52.5 wt % HDPE 1/15.75 wt % HDPE 3/30 wt % Tie Resin 2/1.75 wt % UHMWPE, was melt extruded over a PTFE mandrel to an OD of 1.780 mm and a wall thickness of 0.038 mm. The polyethylene tubes were used to build a catheter and tested for bondability using the methods described above. The inner and outer surfaces of the polyethylene tubing samples were also tested on FTIR. The average values are reported in Table 3.

Example 15

Polyethylene blend tubing with 18 wt % HDPE 1/80 wt % Tie Resin 2/2 wt % UHMWPE, was melt extruded to an OD of 1.830 mm and a wall thickness of 0.041 mm. The polyethylene tubes were used to build a catheter and tested for bondability using the methods described above. The average values are reported in Table 3.

Polyethylene Blend Comparative Examples

Comparative Example 1

Polyethylene blend tubing with 89 wt % HDPE 1/9 wt % LDPE/2 wt % UHMWPE, was melt extruded to an OD of 1.830 mm and a wall thickness of 0.025 mm. Testing for the tubes was conducted using the methods described above. The average values are reported in Table 2. The polyethylene tubes were also used to build a catheter and tested for bondability using the methods described above. The inner and outer surfaces of the polyethylene tubing samples were also tested on FTIR. The average values are reported in Table 3.

Comparative Example 2

Polyethylene blend tubing with 70 wt % HDPE 1/20 wt % HDPE 2/10 wt % Tie Resin, was melt extruded to an OD of 1.850 mm and a wall thickness of 0.025 mm. Testing for the tubes was conducted using the methods described above. The average values are reported in Table 2.

Comparative Example 3

Polyethylene blend tubing with 50 wt % HDPE 1/50 wt % HDPE 3, was melt extruded to an OD of 1.850 mm and a wall thickness of 0.036 mm. Testing for the tubes was conducted using the methods described above. The average values are reported in Table 2.

Comparative Example 4

Polyethylene blend tubing from Comparative Example 3 was irradiated with ebeam for total dosage of 10 MGy. Testing for the tubes was conducted using the methods described above. The average values are reported in Table 2.

Comparative Example 5

Polyethylene blend tubing with 70 wt % HDPE 1/30 wt % Tie Resin 2, was melt extruded to an OD of 1.830 mm and a wall thickness of 0.036 mm. The polyethylene tubes were used to build a catheter and tested for bondability using the methods described above. The average values are reported in Table 3.

Comparative Example 6

Polyethylene blend tubing with 20 wt % HDPE 1/80 wt % Tie Resin 2, was melt extruded to an OD of 1.780 mm and a wall thickness of 0.038 mm. The polyethylene tubes were used to build a catheter and tested for bondability using the methods described above. The average values are reported in Table 3.

Polyethylene Blend Plaque Examples

Plaques Example 1

Polyethylene plaques of 100% HDPE 1 were prepared by melt pressing the resin to a thickness of 0.200 mm at a temperature of 175° C. A PTFE release sheet was used on one side and a stainless steel (SS) release sheet was used on the other. Both surfaces of the plaques were tested by FTIR and contact angle. The results are reported in Table 4.

Plaques Example 2

Polyethylene blend plaques of 90% HDPE 1/10% Tie Resin 1 were prepared using the method described in plaques example 1. Both surfaces of the plaques were tested by FTIR and contact angle. The results are reported in Table 4.

Plaques Example 3

Polyethylene blend plaques of 50% HDPE 1/50% Tie Resin 1 were prepared using the method described in plaques example 1. Both surfaces of the plaques were tested by FTIR and contact angle. The results are reported in Table 4.

TABLE 1

Summary of Polyethylene Resins Used

| Resin ID | Resin Grade | MFI (g/10 min) | Density (g/cm$^3$) |
|---|---|---|---|
| HDPE 1 | Bormed ™ HE7541 | 4.0 | 0.954 |
| HDPE 2 | Ineos K44-24-122 | 0.3 | 0.944 |
| HDPE 3 | Bormed ™ HE2581 | 0.3 | 0.958 |
| LDPE | Bormed ™ LE6600 | 1.5 | 0.919 |
| Tie Resin 1 | Bynel ™ 4104 | 1.1 | 0.930 |
| Tie Resin 2 | Orevac ® 18300M | 2.3 | 0.910 |
| UHMWPE | Mipelon ™ PM 200 | — | 0.940 |

TABLE 2

Summary of Polyethylene Blend Tubing Test Results

| Properties | | Ex. 1 | Ex. 2 | Ex. 3 | Ex. 4 | Ex. 5 | Ex. 6 | Comp. Ex. 1 | Comp. Ex. 2 | Comp. Ex. 3 | Comp. Ex. 4 |
|---|---|---|---|---|---|---|---|---|---|---|---|
| COF | 23° C. | 0.11 | 0.16 | 0.19 | 0.19 | 0.32 | 0.18 | 0.19 | 1.03 | 0.26 | 0.36 |
| | 40° C. | 0.12 | 0.14 | 0.19 | 0.19 | — | 0.15 | 0.19 | 0.92 | 0.30 | — |
| COF in Saline | 23° C. | 0.08 | 0.07 | 0.08 | 0.08 | 0.08 | 0.07 | 0.09 | 0.22 | 0.10 | 0.07 |
| | 40° C. | 0.07 | 0.06 | 0.08 | 0.08 | — | 0.06 | 0.06 | 0.19 | 0.10 | — |
| Storage Modulus (×10$^6$ Pa) | 23° C. | 775 | 780 | 700 | 750 | 710 | 625 | 800 | 580 | 937 | 950 |
| | 40° C. | 575 | 600 | 530 | 550 | 530 | 480 | 600 | 410 | 710 | 730 |
| Tensile Modulus (×10$^6$ Pa) | 23° C. | 670 | 780 | 690 | 550 | 710 | 760 | 580 | 330 | 745 | 940 |
| Stress @ Break (×10$^6$ Pa) | 23° C. | 26.2 | 30.7 | 23.5 | 31.0 | 17.8 | 27.6 | 31.7 | 33.1 | 38.6 | 31.4 |
| Strain @ Break (%) | 23° C. | 580 | 620 | 510 | 530 | 30 | 600 | 670 | 750 | 750 | 850 |
| Contact Angle (°) | ID | — | — | 102 | — | — | 101 | 99 | 107 | 95 | — |
| | OD | — | — | 105 | — | — | 97 | 92 | 108 | 96 | — |
| MFI (g/10 min) | | 1.94 | 2.74 | 1.58 | 0.94 | — | 1.17 | 2.28 | 2.40 | 1.20 | — |
| Calculated Density (g/cm$^3$) | | 0.949 | 0.953 | 0.951 | 0.956 | — | 0.947 | 0.950 | 0.950 | 0.956 | — |
| Surface Roughness | Average Roughness Ra (μm) | 29.49 | 22.02 | 26.94 | 35.83 | — | 42.08 | 26.93 | 8.74 | 8.06 | — |
| | Root Mean Square Rq (μm) | 40.01 | 29.06 | 37.21 | 47.73 | — | 58.00 | 37.38 | 10.84 | 10.07 | — |
| | Maximum Peak Ry (μm) | 192.95 | 153.74 | 175.34 | 225.35 | — | 265.01 | 192.65 | 55.02 | 53.38 | — |

It can be seen that incorporating UHMWPE and/or tie resin lowers COF in saline and is comparable to COF of PTFE (around 0.07). The COF of the PE blends tubing does not change significantly at ambient temperature and 40° C.

TABLE 3

Summary of Polyethylene Blend Catheter Test Results

| Properties | | Ex. 7 | Ex. 8 | Ex. 9 | Ex. 10 | Ex. 11 | Ex. 12 | Ex. 13 | Ex. 14 | Ex. 15 | Comp. Ex. 1 | Comp. Ex. 5 | Comp. Ex. 6 |
|---|---|---|---|---|---|---|---|---|---|---|---|---|---|
| Avg. Load (N) | | 0.658 | 0.596 | 0.974 | 0.894 | 0.627 | 0.667 | 1.214 | 0.903 | 1.423 | 0.427 | 0.654 | 1.267 |
| Avg. Load/Width (N/m) | | 206.3 | 188.4 | 309.1 | 287.5 | 193.9 | 211.4 | 380.7 | 271.9 | 449.2 | 135.7 | 207.5 | 397.7 |
| FTIR ($h_{1780}$/$h_{1460}$) | ID | | 0.0218 | | 0.0347 | | | 0.0301 | 0.0344 | | 0.0237 | | |
| | OD | | 0.0211 | | 0.0403 | | | 0.0286 | 0.0363 | | 0.024 | | |
| FTIR - ID and OD Difference | | | 3% | | 15% | | | 5% | 5% | | 1% | | |

This data demonstrates that bond strength for samples with UHMWPE and tie-resins was higher than samples with only tie-resin and no UHMWPE.

TABLE 4

Summary of Polyethylene Blend Plaque Test Results

|  |  | Plaques Ex. 1 | Plaques Ex. 2 | Plaques Ex. 3 |
|---|---|---|---|---|
| Contact Angle (°) | PTFE | 104 | 99.5 | 84 |
|  | SS | 108 | 69.5 | 84.5 |
| Contact Angle – ID and OD Difference |  | 3.8% | 35% | 0% |
| FTIR ($h_{1780}/h_{1460}$) | PTFE | 0.0207 | 0.0205 | 0.0316 |
|  | SS | 0.0209 | 0.0236 | 0.0294 |
| FTIR – ID and OD Difference |  | 0% | 14% | 6% |

The data from the plaques (Table 4) shows that tie-resin has higher affinity for stainless steel. This could be used to make tubing with more selective distribution of tie-layer on inner and outer surfaces of the tubing. Example 11 indicates that, if the PE blends tubing is extruded over a PTFE core, then there is more tie-resin on the OD layer vs ID layer as seen by the difference in the FTIR absorbance.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A tube comprising a blend of three or more polyethylenes, the tube having an average wall thickness of 0.1 mm or less, and the tube comprising a blend of:
   a first polyethylene that is UHMWPE, in an amount of no more than 20 percent by weight; and
   a second polyethylene comprising at least one chemically modified polyethylene, in an amount of no more than 50 percent by weight; and
   a third polyethylene that is at least one polyethylene resin selected from the group consisting of LLDPE, LDPE, MDPE and HDPE, in an amount of no less than 30 percent by weight of the blend,
   wherein the tube exhibits a tensile modulus value of $550 \times 10^6$ Pa or greater at 23° C.

2. The tube of claim 1, in the form of a tube over a wire or mandrel.

3. The tube of claim 1, wherein the average wall thickness of the tube is less than 0.075 mm.

4. The tube of claim 1, wherein the average wall thickness of the tube is less than 0.050 mm.

5. The tube of claim 1, wherein the tube comprises no more than 10 percent by weight UHMWPE.

6. The tube of claim 1, wherein the tube comprises no more than 5 percent by weight UHMWPE.

7. The tube of claim 1, wherein the third polyethylene resin comprises HDPE.

8. The tube of claim 1, further comprising one or more additives selected from the group consisting of one or more antioxidants, antimicrobials, processing aids, colorants, slip aids, and combinations thereof.

9. The tube of claim 1, wherein the tube exhibits a coefficient of friction in air at 23° C. of 0.2 or less.

10. The tube of claim 1, wherein the tube exhibits a coefficient of friction in saline at 23° C. of 0.2 or less.

11. The tube of claim 1, wherein the tube exhibits a coefficient of friction in saline at 23° C. of 0.1 or less.

12. The tube of claim 1, wherein the at least one chemically modified polyethylene is maleic anhydride grafted polyethylene.

13. The tube of claim 12, wherein the at least one chemically modified polyethylene is selected from an ethylene vinyl acetate copolymer, ethylene methyl acrylate copolymer, ethylene acrylic acid copolymer, ethylene methacrylic acid copolymer, ethylene-acrylic ester-maleic anhydride terpolymer, and combinations thereof.

14. The tube of claim 1, wherein the tube further comprises a continuous layer on an inside surface or an outer surface, the continuous layer comprising a second blend, wherein the second blend comprises a chemically modified polyethylene.

15. The tube of claim 14, wherein the tube comprises a first continuous layer on the inside surface and a second continuous layer on the outer surface, the first and second continuous layers being the same or different.

16. A medical device comprising the tube of claim 1.

17. A method of preparing the tube of claim 1, comprising:
   providing the two or more polyethylenes; and
   extruding the two or more polyethylenes through an extruder to form the tube.

18. The method of claim 17, wherein the two or more polyethylenes are individual components that are combined immediately prior to the extruding.

19. The method of claim 17, wherein the two or more polyethylenes are in the form of a blended material.

20. The method of claim 19, wherein the blended material has an MFI of 3.0 g/10 min or less.

21. The method of claim 19, wherein the blended material has an MFI of 2.5 g/10 min or less.

22. The method of claim 19, wherein the blended material has a calculated density of 0.94 g/cm$^3$ to 0.96 g/cm$^3$.

* * * * *